United States Patent [19]

Williams et al.

[11] Patent Number: 5,202,124
[45] Date of Patent: Apr. 13, 1993

[54] ATTRACTANTS FOR THE ROSE CHAFER, MACRODACTYLUS SUBSPINOSUS (F.), CONTAINING α-IONONE

[75] Inventors: Roger N. Williams, Wooster; Dan S. Fickle, Burbank, both of Ohio; Terrence P. McGovern, deceased, Bowie, Md., by Mary Jo McGovern, sole heir

[73] Assignee: The United States of America as represented by the Secretary of Agriculture, Washington, D.C.

[21] Appl. No.: 626,937

[22] Filed: Dec. 13, 1990

[51] Int. Cl.$^5$ .............................................. A01N 25/00
[52] U.S. Cl. ..................................... 424/405; 424/84; 424/409
[58] Field of Search ........................... 424/405, 409, 84

[56] References Cited

U.S. PATENT DOCUMENTS

| | | | |
|---|---|---|---|
| 3,931,413 | 1/1976 | Frick et al. | 514/557 |
| 4,877,607 | 10/1989 | McGovern et al. | 424/84 |
| 4,880,624 | 11/1989 | Metcalf et al. | 424/84 |

OTHER PUBLICATIONS

Williams et al., J. Econ. Entomol. 83:111–116 (1990).
M. F. Ryan et al., possible role for naturally occurring chemicals in the biological control of correct fly.
Duggan, J. J. (editor) Proceedings of Seminar on Biological Control Feb. 17, 18, 1977.
R. N. Williams and K. V. Miller, Field Assay to Determine Attractiveness of Various Aromatic Compounds to Rose Chafer Adults, J. Econ. Entomol. 75: 196–198 (1982).
R. N. Williams, T. P. McGovern, and M. Klein, Evaluation of Aromatic Compounds and Virgin Females as Attractants for Rose Chafer, Research Circular 272, Fruit Crops, pp. 33–40 (1982).
R. N. Williams, T. P. McGovern, M. G. Klein, and D. S. Fickle, Rose Chafer (Coleoptera: Scarabaeidae): Improved Attractants for Adults, J. Econ. Entomol. 83: 111–116 (1990).
Takeshi Sugimoto and Hiroshi Kameoka, Insect Repellents Containing Eugenol and/or *beta*-Ionone for *Thrips palmi.*"Jpn. Kokai Tokkyo Koho JP 02 49,703 [90 49,703] Appl 88/202,062, " 5 pp. (Aug. 11, 1988); Chemical Abstracts 113: Abstr. 19495p (1990).

*Primary Examiner*—Thurman K. Page
*Assistant Examiner*—Robert H. Harrison
*Attorney, Agent, or Firm*—M. Howard Silverstein; Randall E. Deck; John D. Fado

[57] ABSTRACT

Compositions of α-ionone were found to effectively attract rose chafers, *Macrodactylus subspinosus* (F.). The α-ionone may be used alone or in combination with one or more low-molecular-weight organic compounds including: (1) an organic acid component selected from the group of valeric acid, hexanoic acid, and mixtures thereof, (2) an ester component comprising octyl butyrate, and/or (3) an alcohol component comprising one or more higher alcohols. By attracting the beetles to field traps, the attractants are useful for the monitoring and control of these agricultural pests.

21 Claims, No Drawings

ATTRACTANTS FOR THE ROSE CHAFER, MACRODACTYLUS SUBSPINOSUS (F.), CONTAINING α-IONONE

BACKGROUND OF THE INVENTION

1. Field of the Invention

The rose chafer, *Macrodactylus subspinosus* (F.) is a serious pest of fruit crops, ornamentals, and flowers in eastern North America. Grapevines are a favorite food of the beetles. They begin their attack at blossom time and devour blossoms and newly set fruit, often destroying an entire crop. Other known host plants are peony, rose, blackberry, raspberry, pear, apple, plum, cherry, corn, Scots pine, and many ornamentals. At present, there is no attractant used for monitoring and possibly controlling adult chafers. This invention relates to compositions that are strongly attractive to rose chafers.

2. Description of the Prior Art

Trapping of the rose chafer was first reported by Johnson [Conn. Agr. Exp. Sta. Bull. 434: 314 (1940)]; however, the attractant used was not named. Williams et al. [J. Econ. Entomol. 75: 196-198 (1982)] disclose that valeric acid and hexanoic acid (caprioc acid) are individually attractive to the rose chafer. They also teach that a binary mixture of eugenol and hexanoic acid is attractive to the chafer, but that the attraction of the mixture is due to hexanoic acid alone and that there is no advantage to using the mixture. Williams et al. [Research Circular 272, Fruit Crops, pp. 38-40 (1982)] also tested a large number of acids, anhydrides, acid chlorides, and aldehydes individually as chafer attractants, but none were found superior to valeric acid and hexanoic acid.

SUMMARY OF THE INVENTION

We have now surprisingly found that compositions including α-ionone are potent attractants for the rose chafer, *Macrodactylus subspinosus* (F.). The α-ionone may be used alone, or in combination with one or more certain simple, low-molecular-weight aliphatic organic compounds including: (1) an organic acid component selected from the group of valeric acid, hexanoic acid, and mixtures thereof, or (2) an ester component comprising octyl butyrate, or (3) an alcohol component comprising one or more higher alcohols, or (4) mixtures thereof.

In accordance with this discovery, it is an object of the invention to provide new compositions for attracting rose chafers as an aid to insect control measures.

Another object of the invention is to provide a means for increasing the effectiveness of insect traps for monitoring or suppressing rose chafer populations.

Other objects and advantages of this invention will become obvious from the ensuing description.

DETAILED DESCRIPTION OF THE INVENTION

According to this invention, there is provided a composition for attracting the rose chafer, *Macrodactylus subspinosus*, which includes α-ionone. While the α-ionone may be used alone, in the preferred embodiment insect attraction is substantially increased when the α-ionone is used in combination with one or more low-molecular-weight aliphatic organic compounds including: (1) an organic acid component selected from the group of valeric acid, hexanoic acid, and mixtures thereof, (2) an ester component comprising octyl butyrate, (3) an alcohol component comprising one or more higher alcohols, or (4) mixtures of these acid, ester and/or alcohol components. The preferred alcohols are 7- to 10-carbon, primary, straight-chain alcohols, especially trans-2-nonenol (trans-2-nonen-1-ol), 1-octanol, and 1-nonanol. Other alcohols, such as secondary alcohols and unsaturated alcohols, can also be used.

The α-ionone compositions encompassed herein are effective in controlling a variety of insects. While the pest of particular importance for treatment according to the invention is the rose chafer, other insects including Scarab beetles and Hymenoptera such as honeybees, wasps, carpenter bees, etc., are effectively attracted to the compositions.

Suitable formulations of the α-ionone include α-ionone in crude or impure form, or in substantially pure form. However, as a practical matter, it is expected that substantially pure α-ionone will be formulated with an inert carrier, and optionally with the above-noted acid, ester, and/or alcohol components, for use as an insect attractant composition. The practitioner skilled in the art will recognize that the α-ionone and these acid, ester and/or alcohol components may be formulated in a single or separate compositions. Alternatively, the α-ionone composition may be further formulated with other insect attractants such as pheromones, insect extracts containing pheromones, or host plant volatiles, or with anti-oxidants such as 765 Tinuvin (Ciba Geigy Corp., Hawthorne, N.Y.).

The amount of α-ionone is selected to provide an effective attraction of the insects. The effective amount is defined as that quantity of attractant that attracts the insects to the location of a bait at a rate significantly higher than the attraction to a nonbaited location. Effective concentrations of the α-ionone in the composition may vary between about 0.1 and 99.9%. Suitable amounts and concentrations may be readily determined by the practitioner skilled in the art, and will of course vary with the size of the area to be treated; environmental conditions such as temperature, humidity, and wind conditions; the type of vehicle or carrier; and the insect population. When employed in combination with the above-noted acid, ester and/or alcohol components, the ratio and absolute amounts of all active ingredients may also vary and are similarly selected to provide an effective attraction of the insects to the composition.

The α-ionone of this invention is readily available from commercial sources, and is currently used in perfumes. The aliphatic acids, esters, and alcohols contemplated by the invention are also available from commercial sources.

The attractants may be used in a number of ways, such as in combination with an effective amount of a pesticide to kill the target insects, and in traps to monitor population changes. Precise monitoring will enable growers to reduce the number of insecticide applications when populations are low. Other formulations and methods of use will be obvious to those in the art. In practice, an attractant is used as a trap bait or is otherwise applied to the locus of or in the vicinity of infestation in an amount effective to attract the beetle. As above, an effective amount is defined as that quantity of attractant that attracts the insects to the location of a bait at a rate significantly higher than the attraction to a nonbaited location. Factors such as population density, precipitation, temperature, wind velocity, and release rate will influence the actual number of beetles trapped.

It is envisioned that the attractants would be effective in monitoring or controlling insect and especially beetle populations when used in conjunction with any type of appropriate trap or attractant disseminator as known in the art. The attractant can be disseminated by any suitable means such as by impregnation of wicking material or by use of a deodorant dispenser. Further, the components of the attractant may be combined in a single dispenser provided within a single trap, or provided separately in a plurality of dispensers, all within a single trap. The attractant can be applied to the device undiluted, or volatilization can be controlled or retarded by inclusion of an oleaginous extender such as trioctanoin. Trioctanoin alone is unattractive to the rose chafer. Controlled, slow release may also be effected by encapsulation or absorption into a porous substrate.

The following examples are intended only to further illustrate the invention and are not intended to limit the scope of the invention, which is defined by the claims.

EXAMPLE 1

The attraction of rose chafers toward α-ionone as compared with various other treatments was established under field conditions. The field test was conducted in a sandy field adjacent to a Concord vineyard located near North Kingsville, Ohio, in an area known for very high populations of rose chafers. The test materials, including ionone, listed in Table I were exposed by saturating deodorant dispensers, Loral Poly-Cons (Trece, Inc., Salinas, Calif.), with about 5 ml of the candidate lure. A single opened dispenser was placed inside the perforated attractant dispenser of a metal Japanese beetle trap fitted with a collector for holding beetles. Each lure was replicated over time, with three collection dates used as replicates and one replicate/three day trapping period. Tests were conducted as a randomized complete-block design in which the traps were suspended from steel rods 1 m above ground and spaced in rows 8 m apart. Traps within a row were 10 m apart. Beetle catches were recorded at the end of each trapping period of 3 days. An untreated control was included in all tests. Data were subjected to analysis of variance, and means were compared by Duncan's [Biometrics 11: 1–42 (1955)] multiple range test ($P \leq 0.05$).

EXAMPLE 2

The procedure of Example 1 was repeated at Castalia, Ohio, with the test materials listed in Table II, except that each lure was replicated four times in a randomized complete-block design, and beetle catches were recorded at the end of each trapping period of 3 or 4 days. Traps were also rebaited after each trapping period (3 or 4 days). The data indicate that compositions including α-ionone are significantly more attractive than other related compounds or attractants (i.e., 1-nonanol+octyl butyrate+hexanoic acid+valeric acid).

EXAMPLES 3–5

Selected Mixtures

The procedure of Example 2 was subsequently repeated on three separate occasions at North Kingsville, Ohio, with the lure formulations listed in Tables III–V, except that the α-ionone component of treatment numbers 26 and 27 in Table III was provided in a separate dispenser from the other components, for a total of two dispensers within a single trap. The formulations including α-ionone had the highest means catch per trap, and formulations of α-ionone with hexanoic acid and/or valeric acid, octyl-butyrate and an alcohol (especially trans-2-nonanol) were particularly effective as attractants for the rose chafer.

It is understood that the foregoing detailed description is given merely by way of illustration and that modifications and variations may be made therein without departing from the spirit and scope of the invention.

TABLE I

| Treatment No. | Candidate Lure | Mean No. of Beetles Captured by a Single Trap |
| --- | --- | --- |
| 1 | Dihydro-alpha-ionone | 79.00 a |
| 2 | Tetrahydroionol | 28.33 a |
| 3 | Tetrahydroionyl acetate | 21.67 a |
| 4 | Alpha-ionyl acetate | 49.33 a |
| 5 | Beta-ionyl acetate | 18.00 a |
| 6 | Alpha-ionone | 2450.67 c |
| 7 | Alpha-ionol | 250.33 ab |
| 8 | Beta-ionone | 90.67 a |
| 9 | Beta-ionol | 86.33 a |
| 10 | Valeric acid + hexanoic acid + octyl butyrate + 1-nonanol (Std.) 1:1:1:1 | 760.33 b |
| 11 | Control (untreated) | 28.33 a |

Means followed by the same letter in the same column are not significantly different as determined by Duncan's multiple range test ($P \leq 0.05$).

TABLE II

| Treatment No. | Candidate Lure | Beetles Collected Ratio | Beetles Collected Mean |
| --- | --- | --- | --- |
| 1 | Beta-ionone + valeric acid | 1:1 | 30.40 c |
| 2 | Alpha-ionone + valeric acid | 1:1 | 1241.60 a |
| 3 | Beta-ionol + valeric acid | 1:1 | 47.60 c |
| 4 | Alpha-ionol + valeric acid | 1:1 | 878.80 ab |
| 5 | 1-Nonanol + octyl butyrate + hexanoic acid + valeric acid | 1:1:1:1 | 276.80 bc |
| 6 | Check (untreated) | — | 81.40 bc |
| 7 | Alpha-ionone | single | 1473.20 a |

Means followed by the same letter in the same column are not significantly different as determined by Duncan's multiple range test ($P \leq 0.05$).

TABLE III

| Treatment No. | Candidate Lure | Ratio | Beetles Collected (Entire Season) Mean |
| --- | --- | --- | --- |
| 1 | Control (untreated) | — | 89.00 hi |
| 2 | Hexanoic acid | single | 102.50 hi |
| 3 | Valeric acid | single | 154.75 fghi |
| 4 | Hexanoic acid + valeric acid | 1:1 | 109.50 ghi |
| 5 | Hexanoic acid + 1-nonanol | 1:1 | 130.50 ghi |
| 6 | Octyl butyrate | single | 185.50 fghi |
| 7 | Alpha-ionol | single | 163.50 fghi |
| 8 | Alpha-ionol + hexanoic acid | 1:1 | 241.75 fghi |
| 9 | Alpha-ionol + valeric acid | 1:1 | 203.25 fghi |
| 10 | Beta-ionone | single | 74.50 hi |
| 11 | Beta-ionol | single | 35.75 i |

TABLE III-continued

| Treatment No. | Candidate Lure | Ratio | Beetles Collected (Entire Season) Mean |
|---|---|---|---|
| 12 | Beta-ionone + beta-ionol | 1:1 | 50.50 i |
| 13 | Alpha-ionone | single | 634.25 bcde |
| 14 | Alpha-ionone + hexanoic acid | 1:1 | 892.75 b |
| 15 | Alpha-ionone + valeric acid | 1:1 | 459.50 cdefg |
| 16 | Alpha-ionone + trans-2-nonenol | 1:1 | 414.75 cdefgh |
| 17 | Alpha-ionone + cis-2-nonenol | 1:1 | 347.75 defghi |
| 18 | Alpha-ionone + alpha-ionol | 1:1 | 331.25 defghi |
| 19 | Alpha-ionone + hexanoic acid + valeric acid | 1:1:1 | 698.25 bc |
| 20 | Alpha-ionone + hexanoic acid + valeric acid + octyl butyrate + trans-2-nonenol | 1:1:1:1:1 | 1305.00 a |
| 21 | trans-2-nonenol | single | 111.75 ghi |
| 22 | trans-2-nonenol + hexanoic acid | 1:1 | 314.00 efghi |
| 23 | trans-2-nonenol + valeric acid | 1:1 | 415.75 cdefgh |
| 24 | trans-2-nonenol + hexanoic acid + valeric acid | 1:1:1 | 632.75 bcde |
| 25 | trans-2-nonenol + hexanoic acid + valeric acid + octyl butyrate | 1:1:1:1 | 493.50 cdef |
| 26 | (Alpha-ionone) + (trans-2-nonenol) | 1:1 | 596.50 bcde |
| 27 | (Alpha-ionone) + (hexanoic acid + valeric acid + octyl butyrate + trans-2-nonenol) | 1:1:1:1:1 | 664.25 bcd |
| 28 | Hexanoic acid + valeric acid + octyl butyrate + 1-nonanol | 1:1:1:1 | 321.75 defghi |

Means followed by the same letter in the same column are not statistically different as determined by Duncan's multiple range test ($P \leq 0.05$).

TABLE IV

| Treatment No. | Candidate Lure | Ratio | Mean No. of Beetles/ Trapping Period (Entire Season) |
|---|---|---|---|
| 12 | Alpha-ionone + hexanoic acid | 1:1 | 249.63 a |
| 20 | Alpha-ionone + hexanoic acid + valeric acid + trans-2-nonenol | 1:1:1:1:1 | 239.75 ab |
| 9 | Alpha-ionone + 1% 765 Tinuvin | 1:1 | 197.13 abc |
| 18 | Alpha-ionone + hexanoic acid + valeric acid | 1:1:1 | 194.75 abc |
| 21 | Alpha-ionone + hexanoic acid + valeric acid + octyl butyrate + 1-nonanol | 1:1:1:1:1 | 194.63 abc |
| 19 | Alpha-ionone + hexanoic acid + valeric acid + octyl butyrate | 1:1:1:1 | 192.38 abc |
| 15 | Alpha-ionone + trans-2-nonenol | 1:1 | 179.88 abc |
| 16 | Alpha-ionone + octyl butyrate | 1:1 | 173.75 abc |
| 13 | Alpha-ionone + valeric acid | 1:1 | 172.13 abc |
| 10 | Alpha-ionone (75%) + trioctanoin (25%) | 3:1 | 162.00 abcd |
| 17 | Alpha-ionone + octyl butyrate + trans-2-nonenol | 1:1:1 | 151.50 abcde |
| 14 | Alpha-ionone + 1-nonanol | 1:1 | 151.25 abcde |
| 22 | Hexanoic acid + valeric acid + octyl butyrate + trans-2-nonenol | 1:1:1:1 | 136.63 bcdef |
| 8 | Alpha-ionone | single | 116.75 cdef |
| 11 | Alpha-ionone (50%) + trioctanoin (50%) | 1:1 | 106.75 cdef |
| 23 | Hexanoic acid + valeric acid + octyl butyrate + 1-nonanol | 1:1:1:1 | 87.25 cdef |
| 2 | Hexanoic acid | single | 56.75 def |
| 7 | trans-2-nonenol | single | 47.50 ef |
| 3 | Valeric acid | single | 41.75 f |
| 5 | Octyl butyrate | single | 40.13 f |
| 1 | Control (untreated) | — | 36.50 f |
| 4 | Hexanoic acid + valeric acid | 1:1 | 34.00 f |
| 6 | 1-Nonanol | single | 26.75 f |

Means followed by the same letter in the same column are not statistically different as determined by Duncan's multiple range test ($P \leq 0.05$).

TABLE V

| Treatment No. | Candidate Lure | Ratio | Mean No. of Beetles/ Trapping Period (Entire Season) |
|---|---|---|---|
| 18 | Valeric acid + hexanoic acid + octyl butyrate + trans-2-nonenol + alpha-ionone | 1:1:1:1:1 | 238.75 a |
| 22 | Valeric acid + hexanoic acid + octyl butyrate + trans-2-nonenol + alpha-ionone | 1:1:1:9:1 | 209.75 ab |
| 23 | Valeric acid + hexanoic acid + octyl butyrate + trans-2-nonenol + alpha-ionone | 1:1:1:1:9 | 197.88 abc |
| 19 | Valeric acid + hexanoic acid + octyl butyrate + trans-2-nonenol + alpha-ionone | 9:1:1:1:1 | 180.25 abcd |
| 20 | Valeric acid + hexanoic acid + octyl butyrate + trans-2-nonenol + alpha-ionone | 1:9:1:1:1 | 167.88 abcd |
| 16 | Valeric acid + hexanoic acid + octyl butyrate + | 1:1:1:9:1 | 162.00 abcd |

TABLE V-continued

| Treatment No. | Candidate Lure | Ratio | Mean No. of Beetles/ Trapping Period (Entire Season) |
|---|---|---|---|
| 2 | Valeric acid + hexanoic acid + octyl butyrate + 1-nonanol + alpha-ionone | 1:1:1:1 | 152.13 abcd |
| 17 | Valeric acid + hexanoic acid + octyl butyrate + 1-nonanol + alpha-ionone | 1:1:1:1:9 | 150.88 abcd |
| 10 | Valeric acid + hexanoic acid + octyl butyrate + trans-2-nonenol | 1:1:9:1 | 148.63 abcd |
| 12 | Valeric acid + hexanoic acid + octyl butyrate + 1-nonanol + alpha-ionone | 1:1:1:1:1 | 141.25 bcde |
| 8 | Valeric acid + hexanoic acid + octyl butyrate + trans-2-nonenol | 9:1:1:1 | 139.88 bcde |
| 9 | Valeric acid + hexanoic acid + octyl butyrate + trans-2-nonenol | 1:9:1:1 | 130.38 bcde |
| 14 | Valeric acid + hexanoic acid + octyl butyrate + 1-nonanol + alpha-ionone | 1:9:1:1:1 | 123.88 bcde |
| 15 | Valeric acid + hexanoic acid + octyl butyrate + 1-nonanol + alpha-ionone | 1:1:9:1:1 | 118.75 bcde |
| 13 | Valeric acid + hexanoic acid + octyl butyrate + 1-nonanol + alpha-ionone | 9:1:1:1:1 | 100.88 cde |
| 7 | Valeric acid + hexanoic acid + octyl butyrate + trans-2-nonenol | 1:1:1:1 | 97.25 de |
| 5 | Valeric acid + hexanoic acid + octyl butyrate + 1-nonanol | 1:1:9:1 | 95.50 de |
| 4 | Valeric acid + hexanoic acid + octyl butyrate + 1-nonanol | 1:9:1:1 | 83.50 de |
| 11 | Valeric acid + hexanoic acid + octyl butyrate + trans-2-nonenol | 1:1:1:9 | 82.63 de |
| 21 | Valeric acid + hexanoic acid + octyl butyrate + trans-2-nonenol + alpha-ionone | 1:1:9:1:1 | 81.75 de |
| 6 | Valeric acid + hexanoic acid + octyl butyrate + 1-nonanol | 1:1:1:9 | 81.00 de |
| 1 | Valeric acid + hexanoic acid + octyl butyrate | 1:1:1 | 49.75 e |
| 3 | Valeric acid + hexanoic acid + octyl butyrate + 1-nonanol | 9:1:1:1 | 47.13 e |
| 24 | Check (untreated) | — | 47.00 e |

Means followed by the same letter in the same column are not statistically different as determined by Duncan's multiple range test ($P \leq 0.05$).

We claim:

1. A composition for attracting insects comprising a mixture of (1) α-ionone, and (2) an organic acid component selected from the group consisting of valeric acid, hexanoic acid and mixtures thereof and wherein the concentration of α-ionone is between about 0.1 and 99.9%.

2. A composition as described in claim 1 further comprising octyl butyrate.

3. A composition as described in claim 1 further comprising an alcohol component comprising one or more higher alcohols.

4. A composition as described in claim 3 wherein said alcohol component comprises at least one straight-chain, aliphatic alcohol.

5. A composition as described in claim 4 wherein said aliphatic alcohol is selected from the group consisting of trans-2-nonenol, 1-octanol, and 1-nonanol.

6. A composition as described in claim 1, further comprising octyl butyrate, and an alcohol component comprising one or more higher alcohols.

7. A composition as described in claim 6 wherein said alcohol component comprises at least one straight-chain, aliphatic alcohol.

8. A composition as described in claim 7 wherein said aliphatic alcohol is selected from the group consisting of trans-2-nonenol, 1-octanol, and 1-nonanol.

9. A composition as described in claim 1 further comprising an inert carrier.

10. A composition as described in claim 1 further comprising a pesticide.

11. A method for attracting insects, comprising the step of providing α-ionone in combination with an organic acid component selected from the group consisting of valeric acid, hexanoic acid, and mixtures thereof, to the locus of said insects, and wherein the concentration of α-ionone is between about 0.1 and 99.9%.

12. A method as described in claim 11 wherein said insects are rose chafer beetles, Macrodactylus subspinosus (F.).

13. A method as described in claim 12 wherein said α-ionone is further provided in combination with octyl butyrate.

14. A method as described in claim 12 wherein said α-ionone is further provided in combination with an alcohol component comprising one or more higher alcohols.

15. A method as described in claim 14 wherein said alcohol component comprises at least one straight-chain, aliphatic alcohol.

16. A method as described in claim 15 wherein said aliphatic alcohol is selected from the group consisting of trans-2-nonenol, 1-octanol, and 1-nonanol.

17. A method as described in claim 11 wherein said α-ionone is provided in combination with an inert carrier.

18. A method as described in claim 11 wherein said α-ionone is provided in combination with a pesticide.

19. A method as described in claim 11, wherein said α-ionone and said organic acid component are combined in a single composition.

20. A method as described in claim 11, wherein said α-ionone and said organic acid component are in separate compositions.

21. A method for attracting rose chafer beetles, Macrodactylus subspinosus (F.), comprising the step of providing α-ionone to the locus of said rose chafer beetles, Macrodactylus subspinosus (F.), in an amount effective to attract said beetles.

* * * * *